United States Patent
Oshino et al.

(10) Patent No.: US 8,591,867 B2
(45) Date of Patent: Nov. 26, 2013

(54) ORAL PREPARATION SYSTEM

(75) Inventors: Kazushi Oshino, Tokyo (JP); Atsushi Yamagishi, Tokyo (JP); Tadayuki Tokunaga, Tokyo (JP); Masanobu Wakasa, Tokyo (JP)

(73) Assignee: Kao Corporation, Tokyo (JP)

( * ) Notice: Subject to any disclaimer, the term of this patent is extended or adjusted under 35 U.S.C. 154(b) by 1561 days.

(21) Appl. No.: 10/540,266

(22) PCT Filed: Dec. 26, 2003

(86) PCT No.: PCT/JP03/17044
§ 371 (c)(1), (2), (4) Date: Dec. 7, 2005

(87) PCT Pub. No.: WO2004/060336
PCT Pub. Date: Jul. 22, 2004

(65) Prior Publication Data
US 2006/0134019 A1    Jun. 22, 2006

(30) Foreign Application Priority Data

Dec. 27, 2002  (JP) ................................. 2002-381820
Sep. 19, 2003  (JP) ................................. 2003-327681

(51) Int. Cl.
| | |
|---|---|
| *A61Q 11/00* | (2006.01) |
| *A61K 8/00* | (2006.01) |
| *A61K 8/18* | (2006.01) |
| *A61K 8/19* | (2006.01) |
| *A61K 8/21* | (2006.01) |
| *A61K 8/24* | (2006.01) |
| *A61K 8/30* | (2006.01) |
| *A61K 8/55* | (2006.01) |

(52) U.S. Cl.
USPC ................ 424/52; 424/49; 424/57; 424/401; 433/215; 433/216; 433/217.1

(58) Field of Classification Search
USPC .................... 424/52, 57, 401; 433/216, 217.1
See application file for complete search history.

(56) References Cited

U.S. PATENT DOCUMENTS

| | | | |
|---|---|---|---|
| 4,080,440 A | 3/1978 | DiGiulio et al. | |
| 4,193,988 A | 3/1980 | Forward et al. | |
| 4,448,766 A | 5/1984 | Morton | |
| 4,460,565 A | 7/1984 | Weststrate et al. | |
| 4,565,691 A | 1/1986 | Jackson | |
| 5,378,131 A | 1/1995 | Greenberg | |
| 5,605,675 A | 2/1997 | Usen et al. | |
| 5,817,296 A * | 10/1998 | Winston et al. | 424/49 |
| 5,858,333 A | 1/1999 | Winston et al. | |
| 5,891,448 A * | 4/1999 | Chow et al. | 424/400 |
| 5,895,641 A | 4/1999 | Usen et al. | |
| 6,159,448 A | 12/2000 | Winston et al. | |
| 6,770,265 B2 * | 8/2004 | Ishihara et al. | 424/49 |

FOREIGN PATENT DOCUMENTS

| | | |
|---|---|---|
| DE | 2 302 330 | 8/1973 |
| DE | 198 34 355 | 2/2000 |
| EP | 0 089 136 | 9/1983 |
| EP | 0 263 638 | 4/1988 |
| JP | 58-219107 | 12/1983 |
| JP | 3-72415 | 3/1991 |
| JP | 6-37382 | 5/1994 |
| JP | 2000-191486 | 7/2000 |

OTHER PUBLICATIONS

U.S. Appl. No. 10/584,142, filed Jun. 26, 2006, Tokunaga, et al.

* cited by examiner

*Primary Examiner* — Lezah Roberts
(74) *Attorney, Agent, or Firm* — Oblon, Spivak, McClelland, Maier & Neustadt, L.L.P.

(57) ABSTRACT

An oral preparation of the present invention contains a multi-composition system including a calcium ion supplying compound; a fluoride ion supplying compound a polyolphosphate ion supplying compound; and, a monofluorophosphate ion supplying compound, wherein the calcium ion supplying compound and the fluoride ion supplying compound are separated within the oral preparation.

15 Claims, 8 Drawing Sheets

Change of turbidity after mixing two agents

Example 1

Comparative
Example 1

Comparative
Example 3

A segment of an incipient caries

ORAL PREPARATION SYSTEM

FIELD OF THE INVENTION

The present invention relates to an oral preparation system which contains a calcium ion supplying compound and a fluoride ion supplying compound.

BACKGROUND OF THE INVENTION

Tooth enamel contains hydroxyapatite as a major component, and usually in the mouth, the elution of phosphate ions or calcium ions from the tooth (i.e. demineralization) and the crystallization of calcium phosphate or hydroxyapatite (i.e. remineralization) are in an equilibrium state. Fluoride ions are able to prevent the tooth from decaying by inhibiting demineralization and by accelerating supply and crystallization of calcium ions and phosphate ions, i.e. remineralization of the tooth. Therefore supply of fluoride ions and calcium ions to the oral cavity makes it possible to accelerate remineralization of the tooth.

However, in the case when fluoride ions and calcium ions are incorporated in the same composition, calcium fluoride precipitates in the composition. Such preformed calcium fluoride is a powdery substance (mean particle size: several micrometers), and when this is supplied to the oral cavity, it will be scarcely adsorbed on the tooth because its particle size is too large, thereby hardly exhibiting an effect of accelerating remineralization of the tooth.

Based on this perspective, there has been proposed an oral preparation in which a calcium ion source and a fluoride ion source are made into separate compositions respectively, then the two compositions are admixed with each other in the mouth or immediately prior to introduction into the mouth, thereby forming calcium fluoride in the oral cavity. For example, there is an oral hygiene product containing a calcium ion source, a fluoride ion source and a calcium sequestering agent (Japanese Patent Laid-Open Nos. Sho 58-219107 and Hei 10-511956). However, since this oral hygiene product contains a calcium sequestering agent, the oral hygiene product has a problem that fluorine adsorption on the tooth is inhibited on the contrary by the calcium sequestering agent.

Moreover, the composition containing calcium fluoride preformed in a colloidal form has also been proposed (Japanese Patent Laid-Open No. Hei 3-72415). However, it has a problem that the stability of the colloid decreases when preserving over a long period, and it thus fails to have an effect enough to deposit calcium fluoride particles on the tooth surface.

Japanese Patent Laid-Open No. Sho 63-101312 discloses that rapid precipitation of calcium fluoride can be induced. In this case, however, it is not possible to control the rate of aggregation of the calcium fluoride particles (the primary particles) after precipitation, so that homo-aggregation after forming the primary particles rapidly progresses to form secondary particles. The secondary particles of calcium fluoride thus formed have a problem that the particle size grows too large and decreases the amount being adsorbed on the tooth.

Here, it is to be noted that the primary particle is the crystal particle of calcium fluoride made from fluoride ions and calcium ions, and the secondary particle is the particle formed by aggregation such as homo-aggregation of the primary particle.

Further, Japanese Patent Laid-Open No. Hei 10-511956 discloses that calcium fluoride formation is controlled in mouth rinses, dentifrices and gels. Namely, in order to control the calcium fluoride formation, it is proposed to contain a calcium fluoride inhibitor which causes to delay precipitation of calcium fluoride for at least about 5 seconds after mixing calcium ions and fluoride ions.

As the result of containing the calcium fluoride inhibitor, a delay of calcium fluoride aggregation (namely, the formation of secondary particle) has been achieved. However, the presence of the inhibitor also inhibits the formation reaction of calcium fluoride (namely, the formation of the primary particle), which causes a problem that the amount of calcium fluoride formation as the primary particle decreases.

Accordingly, in order to attain more efficient acceleration of remineralization, it is desired that the rate of calcium fluoride aggregation (the formation of the secondary particle) can be controlled without affecting calcium fluoride formation (the formation of the primary particle).

SUMMARY OF THE INVENTION

The present invention provides an oral preparation system containing the following components:
(A) a calcium ion supplying compound;
(B) a fluoride ion supplying compound other than a monofluorophosphate ion supplying compound;
(C) a polyolphosphate ion supplying compound; and,
(D) a monofluorophosphate ion supplying compound,
wherein components (A) and (B) are separated within the oral preparation system.

DETAILED DESCRIPTION OF THE INVENTION

Figure 1:
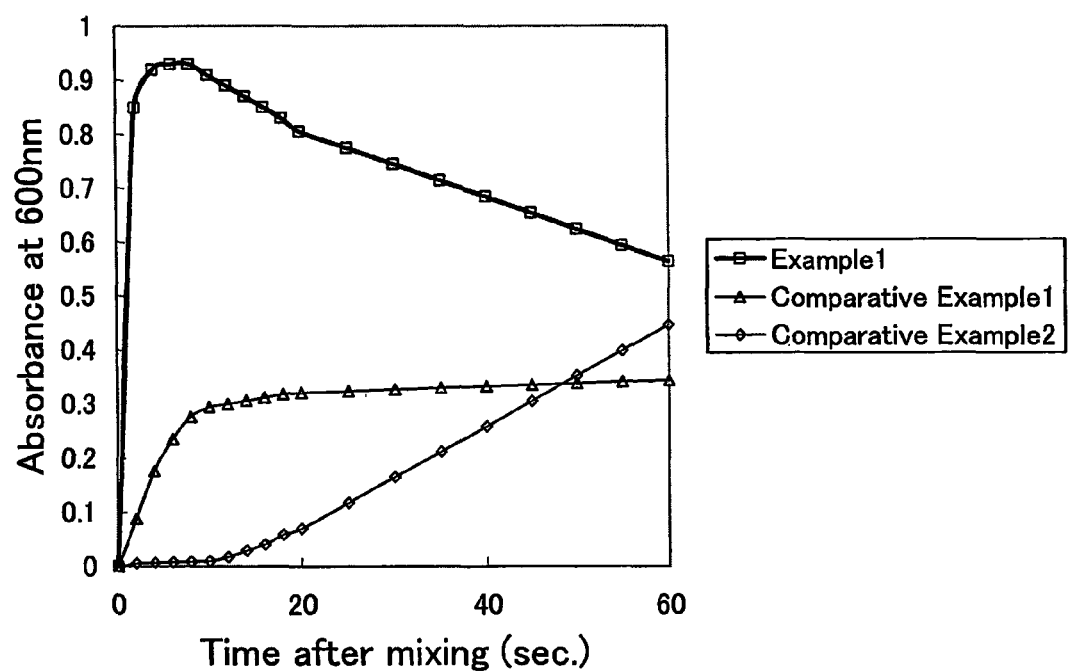
FIG. 1 shows a change of turbidity of solution after mixing two composition, X and Y, in an Example and Comparative Examples.

The present invention provides an oral preparation system which is able to form the primary particles of calcium fluoride and able to control the rate of calcium fluoride aggregation (namely, the formation of secondary particle) and accordingly allows greater adsorption of calcium fluoride fine particles on the tooth or the like, thus being excellent in effects of inhibiting demineralization of the tooth and accelerating remineralization.

The present inventors have found that polyolphosphate ions can control the particle size of the secondary particle of calcium fluoride (a calcium fluoride aggregate) by reducing the size of the primary particle of calcium fluoride to a smaller size and by inhibiting the primary particle aggregation (the formation of a secondary particle), and thereby completing benefits of the present invention.

That is to say, the present inventors could accomplish an oral preparation system that is able to accelerate formation of the primary particle and able to control formation of the secondary particle and thus exhibits excellent effects of inhibiting demineralization of the tooth and accelerating remineralization, by applying, as an oral preparation, a multi-composition system containing (A) a calcium ion supplying compound and (B) a fluoride ion supplying compound, other than a monofluorophosphate ion supplying compound, wherein components (A) and (B) are separated or otherwise not in contact with each other within the oral preparation system. The multi-composition system further contains (C) a polyolphosphate ion supplying compound and (D) a monofluorophosphate ion supplying compound as components to be contained in a composition containing either component (A) or component (B), in both a composition containing component (A) and a composition containing component (B), or in another additional separate composition.

Moreover, the present inventors made it possible to generate calcium fluoride fine particles (a primary particle) rapidly, by mixing component (A), component (B), component (C) and component (D) with each other, such as to make any one of the following combinations in the multi-composition system:

(1) a combination of the composition containing component (A), (C) and (D), and a separate composition containing component (B);

(2) a combination of the composition containing component (A), and a separate composition containing the components (B), (C) and (D);

(3) a combination of the composition containing component (A) and (C), and a separate composition containing components (B) and (D);

(4) a combination of the composition containing component (A) and (D), and a separate composition containing the component (B) and (C);

(5) a combination of the composition containing component (A) and (D), and a separate composition containing (B) and a separate composition containing (C);

(6) a combination of the composition containing component (A) and (C), a separate composition containing component (B), and a separate composition containing component (D);

(7) a combination of the composition containing components (B) and (D), a separate composition containing component (A), and a separate composition containing component (C);

(8) a combination of the composition containing component (B) and (C), a separate composition containing component (A), and a separate composition containing component (D); and (9) a combination of the composition containing component (A), a separate composition containing component (B), a separate composition containing component (C), and a separate composition containing component (D).

The calcium fluoride fine particles has a primary particle size of, preferably from 0.3 to 15 nm (nanometers), more preferably from 0.3 to 12 nm, and even more preferably from 0.3 to 9 nm.

The secondary particle that is aggregate of the calcium fluoride fine particles may contain monofluorophosphates. The content of the monofluorophosphates preferably ranges from 0.05 to 20 wt. % (% by weight) of the aggregate, more preferably from 0.1 to 15 wt. %, and even more preferably from 0.5 to 10 wt. %.

The secondary particle of the calcium fluoride fine particles may also contain polyolphosphates. The content of the polyolphosphates preferably ranges from 0.05 to 20 wt. % of the aggregate, more preferably from 0.1 to 15 wt. %, and even more preferably from 0.5 to 10 wt. %.

Further, the secondary particle of the calcium fluoride fine particles may coincidently contain both the monofluorophosphates and the polyolphosphates, and it may be a composite particle with monofluorophosphates and polyolphosphates. The total content of the monofluorophosphates and the polyolphosphates preferably ranges from 0.1 to 40 wt. % of the composite particle, more preferably from 0.2 to 30 wt. %, and even more preferably from 1 to 20 wt. %.

In the case of using an oral preparation system of the present invention, while more primary particles of calcium fluoride can be formed, the rate of calcium fluoride aggregation (the secondary particle formation) can be controlled, thereby allowing greater adsorption of calcium fluoride fine particles on the tooth or the like. Therefore, the present invention provides an oral preparation system which has benefits such as excellent adsorbability on the surface of the tooth or the like in the oral cavity and excellent effects of inhibiting demineralization and accelerating remineralization of the tooth.

Moreover, use of the oral preparation system of the present invention, which contains polyolphosphates as a component for the multi-composition system, allows the calcium fluoride fine particles and polyolphosphates to be preferably made into composite particles being present in the secondary particle when the secondary particle of calcium fluoride is formed. The oral preparation system can suppress pH decreases of residual plaque (especially, residual plaque after brushing of teeth) by the pH buffering ability of the polyolphosphates contained in said composite particle, thereby preventing dental caries from occurring due to the pH decrease of the plaque. Further, in an embodiment in which the calcium fluoride fine particles and monofluorophosphates are made into composite particles and then such composite particles are present in the secondary particle, the secondary particle is improved in effects of the monofluorophosphates, namely, effects of enhancing inhibition of tooth demineralization and accelerating tooth remineralization. These effects are similarly beneficial to the prevention of the dental caries.

In the case of using an oral preparation system of the present invention, the calcium fluoride can be efficiently adsorbed on the tooth by controlling the particle size of calcium fluoride, thus obtaining excellent effects of inhibiting demineralization and accelerating remineralization of the tooth.

Further, in an embodiment in which the calcium fluoride fine particles, monofluorophosphates and polyolphosphates are made into composite particles and then the composite particles are present in the secondary particle, by a synergy effect between them, pH decrease of the residual plaque is suppressed, demineralization of the tooth is inhibited, and remineralization is accelerated more efficiently, so that prevention of the caries can be achieved more effectively.

Examples of calcium ion supplying compounds which may be used as component (A) of the present invention include calcium polyolphosphate, calcium hydroxide, calcium chloride, calcium acetate, calcium formate, calcium lactate, calcium nitrate, calcium gluconate, calcium benzoate, calcium isobutyrate, calcium propionate, calcium salicylate, calcium carbonate, calcium hydrogenphosphate, calcium phosphate, hydroxyapatite, and mixtures thereof. Examples of calcium polyolphosphate (component (E)) include calcium glycerophosphate, calcium glucose-1-phosphate, and calcium glucose-6-phosphate. In order to improve the taste of the oral preparation system, there may be exemplified, as preferred calcium ion supplying compounds, calcium lactate and calcium glycerophosphate.

The calcium ion supplying compound in component (A) preferably supplies the composition containing component (A) with 10 to 16000 ppm of calcium ions, more preferably 50 to 12000 ppm, and even more preferably 200 to 8000 ppm, from the viewpoint of efficiently forming calcium fluoride in the oral cavity. As a calcium ion supplying compound which may be used in the present invention, it is preferable to use a calcium ion supplying compound capable of being ionized. In a case that the amount used of the composition containing component (A) and the composition containing component (B) are equal in terms of weight, such calcium ion supplying compound is preferably at an amount in a range from 0.25 to 400 µmol/g (micromole/g), more preferably 1.25 to 300 µmol/g, and even more preferably 5 to 200 µmol/g in the composition containing component (A).

Examples of fluoride ion supplying compounds which may be used for component (B) in the present invention include sodium fluoride, stannous fluoride, potassium fluoride, zinc fluoride, betaine fluoride, alanine stannous fluoride, sodium fluorosilicate, hexylamine fluoride and mixtures thereof. There may be exemplified, as preferred fluoride ion supplying compounds, sodium fluoride and stannous fluoride.

The fluoride ion supplying compound in the component (B) preferably supplies the composition containing component (B) with 5 to 4000 ppm of fluoride ions, more preferably 25 to 2000 ppm, and even more preferably 100 to 1000 ppm, from the viewpoint of efficiently forming calcium fluoride in the oral cavity. In order to bring the fluoride ion concentration within the aforementioned range, for example, such fluoride ion supplying compound is preferably contained at an amount in the range from 0.065 to 210 µmol/g, and more preferably from 0.325 to 158 µmol/g, even more preferably from 2.6 to 105 µmol/g in the composition containing component (B), if the amount used of component (A) and component (B) are equal in terms of weight.

Calcium ion and fluoride ion react in the proportion of 1:2 (mole ratio) and form calcium fluoride. It is preferable that the content ratio (mole ratio) of calcium ion supplying compound (expressed in terms of calcium) and fluoride ion supplying compound (expressed in terms of fluorine) in the oral preparation system of the present invention ranges from 1:8 to 4:1, more preferably from 1:4 to 2:1, from the viewpoint of forming calcium fluoride efficiently in use.

Examples of monofluorophosphate ion supplying compounds which may be used as component (D) in the present invention include sodium monofluorophosphate, potassium monofluorophosphate, magnesium monofluorophosphate, calcium monofluorophosphate. A preferred monofluorophosphate ion supplying compound is sodium monofluorophosphate. Monofluorophosphate ion remains in the oral cavity, especially in dental plaque or the like, and is decomposed gradually by phosphatase and the like in saliva or dental plaque, while continually supplying the teeth with fluoride ion. Monofluorophosphate ion is preferably contained in the composition containing component (A) at an amount in a range from 0.065 to 210 µmol/g, more preferably from 0.325 to 158 µmol/g, and even more preferably from 2.6 to 105 µmol/g if component (D) is contained only in the composition containing component (A) and the amount used of the composition containing component (A) and the composition containing component (B) are equal in terms of weight.

The monofluorophosphate ion supplying compound as component (D) may be contained in a composition containing either one of the aforementioned component (A) and the aforementioned component (B), may be contained in both a composition containing component (A) and a composition containing component (B), or may be present as a third component separately from compositions containing component (A) and component (B), or as one component contained in a third composition Examples of polyolphosphate ion supplying compounds which may be used as component (C) in the present invention include, a monosaccharide having 3 to 10 carbon atoms with one or more phosphate groups per molecule, an oligosaccharide consisting of 2 to 6 such monosaccharides, and a polyhydric alcohol having 3 to 10 carbon atoms with one or more phosphate groups per molecule. Specific examples of polyolphosphate ion supplying compounds include glycerophosphoric acid, glyceryl aldehyde 3-phosphate, erythrose 4-phosphate, ribose 5-phosphate, glucose 1-phosphate, glucose 6-phosphate, inositol monophosphate, inositol hexaphosphate, fructose 1-phosphate, fructose 6-phosphate, fructose 1,6-diphosphate, ascorbic acid 2-phosphate, phosphorylated maltotriose, phosphorylated maltotetraose, and salts thereof such as sodium, potassium, calcium, or magnesium salt. Among them, sodium salts or calcium salts of glycerophosphoric acid, glucose 1-phosphate, or glucose 6-phosphate are preferable. As stated above, in the case of containing calcium polyolphosphates (component (E)) such as calcium glycerophosphate, calcium glucose-1-phosphate, and calcium glucose-6-phosphate, it can also serve as the calcium ion supplying compound (component (A)).

The polyolphosphate ion supplying compound as component (C) may be contained in a composition containing either one of the aforementioned component (A) and the aforementioned component (B), may be contained in both a composition containing component (A) and a composition containing component (B), or may be present as a third component separately from compositions containing component (A) and component (B), or as one component contained in a third composition.

In the oral preparation system of this invention, polyolphosphate ion supplying compound as component (C) is preferably at an amount in a range from 0.125 to 200 µmol/g (micromole/g), more preferably 0.625 to 150 µmol/g, and even more preferably 2.5 to 100 µmol/g. In a case that polyolphosphate ion supplying compound as component (C) is contained in a composition containing component (A) and the amount used of the composition containing component (A) and the composition containing component (B) are equal in terms of weight, such polyolphosphate ion supplying compound is preferably at an amount in a range from 0.25 to 400 µmol/g (micromole/g), more preferably 1.25 to 300 µmol/g, and even more preferably 5 to 200 µmol/g in the composition containing component (A).

In a case that calcium polyolphosphate (component (E)) is used as both polyolphosphate ion supplying compound and calcium ion supplying compound, and the amount used of the composition containing component (E) and the composition containing component (B) are equal in terms of weight, such calcium polyolphosphate is preferably at an amount in a range from 0.25 to 400 µmol/g (micromole/g), more preferably 1.25 to 300 µmol/g, and even more preferably 5 to 200 µmol/g in the composition containing component (E).

The oral preparation system of the present invention preferably contains 10 to 70 wt. % of sugar alcohol as the concentration in the mixture in use. Examples of the sugar alcohol include lactitol, isomaltitol, maltotriitol, isomaltotriitol, panitol, isomaltotetraitol, erythritol, arabitol, ribitol, xylitol, sorbitol, mannitol, maltitol and the like. Such sugar alcohol may be either D or L configuration, or mixture thereof.

Moreover, the sugar alcohols preferably contain xylitol, and the content of xylitol in the sugar alcohols is preferably from 1 to 40 wt. %, and more preferably from 2 to 20 wt. %.

In the oral preparation system of the present invention, it is preferable that component (A) and component (B) are put in a container or containers so as not to bring those components (A) and (B) into contact with each other, and that they are mixed in the oral cavity or at a time immediately prior to introduction into the oral cavity.

Moreover, the oral preparation system of the present invention preferably takes a form of a multi-composition system by preserving the component (A) and component (B), and compositions containing component (A) and compositions containing component (B) in a non-contact state until use or just before use of them.

In order to form the multi-composition system, component (A) and component (B) may be put in different containers per composition, or component (A) and component (B) may be put in a sole container in a non-contact state. Examples of the container to put in a non-contact state include a tube inside of which is divided by a partition, a tube in which another tube is inserted, and a container made by joining separate tubes so as to unit the contents at the opening of the container.

The oral preparation system of the present invention may incorporate an anionic surfactant which has been generally used in an oral preparation system, for example, ester salts of alkyl sulfate such as sodium lauryl sulfate, salts of N-acylamino acid such as N-acylsarcosinate salts and the like. Moreover, ingredients which have been generally used in an oral preparation may be added in the oral preparation system of the present invention, and examples of such ingredients include: abrasives such as silicic acid anhydride, calcium hydrogen phosphate, and calcium carbonate; humectants such as glycerin and polyethylene glycol; foaming agents; binding agents such as sodium carboxymethyl cellulose and carageenan; sweetners such as sodium saccharate; coloring agents; preservatives such as methyl parahydroxybenzoate; bactericides such as benzethonium chloride, triclosan, and isopropyl methyl phenol; anti-inflammatory agents such as beta-glycyrrhizin acid, and tocopherol; perfumes; and the like. These ingredients may be contained in both or either one of the composition containing component (A) and the composition containing component (B).

The oral preparation system of the present invention can be used as, for example, tooth powder, lubricating dentifrice, toothpaste, liquid dentifrice, mouthwash, and the like.

EXAMPLES

The following examples further describe and demonstrate embodiments of the present invention. The examples are given solely for the purpose of illustration and are not to be construed as limitations of the present invention.

1. Mouthwashes
(1) Preparation of Mouthwashes

In each of the Examples and Comparative Examples, two compositions, namely composition (X) and composition (Y), were prepared according to compositions as shown in Table 1. Then each of them was put in isolated containers per composition at equal amounts.

(2) Measuring Method a. Observation of the State Regarding Adsorption of the Fine Particles on Hydroxyapatite (HAP)

Composition (X) and composition (Y) in each of the Examples and Comparative Examples shown in Table 1 were mixed with equal amounts. 10 g of HAP powder (available from Wako Pure Chemical Industries, Ltd.) was treated in 1 L of the prepared mixture for 3 minutes, and then washed with deionized water, and dried by vacuum drying, thereby obtaining a powder. The state in which calcium fluoride is adsorbed on the recovered HAP powder was observed by scanning electron microscope (SEM).

A sample of the HAP powder on which calcium fluoride is well adsorbed was judged as "◯", a sample of the HAP powder on which calcium fluoride is adsorbed some was judged as "Δ", and a sample of the HAP powder on which calcium fluoride is little or not adsorbed was judged as "X".

TABLE 1

| | | Composition (wt. %) | | | | | | | | | |
|---|---|---|---|---|---|---|---|---|---|---|---|
| | | Example | | | | Comparative Example | | | | | |
| | | 1 | | 2 | | 1 | | 2 | | 3 | |
| Component | | X | Y | X | Y | X | Y | X | Y | X | Y |
| Calcium glycerophosphate | A, C (=E) | 1 | — | 0.5 | — | — | — | 1 | — | — | — |
| Calcium lactate | A | — | — | 0.5 | — | 1 | — | — | — | — | — |
| Sodium monofluorophosphate | D | 0.7 | — | 0.7 | — | — | — | — | — | 0.7 | — |
| Sodium fluoride | B | — | 0.2 | — | 0.2 | — | 0.2 | — | 0.2 | — | 0.2 |
| Purified water | | *1 | *1 | *1 | *1 | *1 | *1 | *1 | *1 | *1 | *1 |
| Total | | 100 | 100 | 100 | 100 | 100 | 100 | 100 | 100 | 100 | 100 |
| State regarding adsorption of particles | | ◯ | | ◯ | | Δ | | Δ | | X | |
| Amount of fluorine adsorption (mg/m$^2$) | | 33 | | 28 | | 20 | | 14 | | 2 | |

*1: balance b. Quantitative Determination of Amount of Fluorine Adsorption on HAP Pellet In each of the Examples and Comparative Examples, HAP pellet (APP-100; 10×10×2 mm, PENTAX, Japan) was treated in 10 ml of composition (X) for 30 seconds, and then treated in 10 ml of composition (Y) for 30 seconds. These treatments were alternately conducted for 3 minutes. The calcium fluoride particles adsorbed on the surface of the HAP pellet by these treatments were extracted by hydrochloric acid. Using the extracted solution, an amount of fluorine adsorbed on the surface of HAP pellet was determined by means of an ion analyzer (Expandable ion Analyzer EA940 manufactured by ORION) with fluorine ion selective electrode (inplus-Fluoride manufactured by ORION).

c. Potentiometric Titration 0.1 g of HAP powder (control) and respective HAP powders treated by the compositions of Example 1 and Comparative Example 1 shown in the Table 1 were weighed precisely, and 40 ml of deionized water was added to them, thereby preparing the slurries in suspended state. Using automatic potentiometric titrator AT-300 (manufactured by Kyoto Electronics Manufacturing Co., LTD), 0.1N-hydrochloric acid was added dropwise at 0.5 ml by 0.5 ml to the suspended slurry while it was continually stirred with a stirrer, and pH was measured after 5 minutes from every dropping, to obtain the titration curve.

d. Measurement of Size of Calcium Fluoride Primary Particle

For samples of HAP powder (control) and respective HAP powders treated by the compositions of Example 1 and Comparative Example 1 shown in Table 1, 2-theta ($2\theta$) degrees were measured over the range of 2.5 to 75 by powder X-ray diffraction method (instrument: RINT2500VPC (manufactured by Rigaku Corporation), Cu K-alpha, 40 kV, 120 mA, divergence slit: 1 degree, divergence vertical restriction slit: 10 mm, scattering slit: 1.25 mm, receiver slit: 0.3 mm, scan speed: 1.000 degree/min.).

e. Analysis of the Component of Calcium Fluoride Secondary Particle

A HAP powder sample treated by the composition of Example 1 shown in Table 1 was subjected to the deposition treatment by Pt—Pd, and was used as an EDS measurement sample. A measurement of the SEM-EDS (energy-dispersive x-ray analysis method) (instrument: S-4000 (manufactured by Hitachi, Ltd.), condition: electron beam 10 kV/EMAX-3770 (manufactured by HORIBA, Ltd.)) was carried out by UTW mode to check the presence of treated sample.

Moreover, for each of the HAP powder samples treated by the compositions in Example 1 and Comparative Example 1, fluorine (19F) was monitored by mass spectrometry using temperature-programmed desorption method (TPD) (instrument: TPD (manufactured by BEL JAPAN, INC.), 0.1 g of sample, under vacuum, programming rate 10° C./min.).

Further, each of the components in the HAP powder sample treated by the composition of Example 1 was identified and quantitatively determined by ion chromatography. Preparation of the sample was carried out in such manner that 0.1 g of HAP powder sample was precisely weighed in a beaker, 40 ml of extra pure water was poured therein, and 0.5 ml of 0.01 mol/l-hydrochloric acid was added, and then it was stirred for 1 hour. The slurry was filtrated through a membrane filter with 0.45 μm of a pore size. 5 ml of a solution initially filtrated was rejected and a solution subsequently filtrated was used as a solution for measurement of ion chromatography. The ion chromatography was measured by means of DX320 (equipped with EG-40)(manufactured by Dionex Corporation), and in the measurement, monofluorophosphates and glycerophosphates were identified by comparing their retention times with those of reference materials and quantitatively determined from peak area by calibration curve method.

The conditions of quantitative analysis of Monofluorophosphates and glycerophosphates were as follows: separation column, IonPac AS-16 (manufactured by Dionex Corporation); guard column, IonPacAG-16 (manufacturedbyDionex Corporation); elutingsolvent, KOH (usingEG-40); flow rate, 1.0 ml/min; gradient, 10 mmol/l to 70 mmol/l (0 to 20 min.); suppressor, ASRS (200 mA); and detector, conductimetric detector.

(3) Result a. The Amount and the State of Fluorine Adsorption on HAP Pellet

The amount of fluorine adsorption on HAP pellet which was alternately treated by compositions (X) and (Y) in Example 1 as shown in Table 1, in which composition (X) contains calcium glycerophosphate and sodium monofluorophosphate and composition (Y) contains sodium fluoride, was 33 mg/m$^2$.

In other words, in the case of Example 1, the calcium fluoride fine particles (the primary particle) which were formed by sodium monofluorophosphate were inhibited to form the secondary particle by the presence of calcium glycerophosphate, so that the calcium fluoride fine particles in a form of the primary particle can be effectively adsorbed on the HAP pellet, and therefore the amount of fluorine adsorption on the HAP pellet was 33 mg/m$^2$.

Moreover, in the case of Example 2 containing component (A) containing calcium glycerophosphate, calcium lactate, and sodium monofluorophosphate, the amount of fluorine adsorption on the HAP pellet alternately treated composition (X) and composition (Y) was 28 mg/m$^2$.

Both Example 1 and Example 2 could be verified with the state of good adsorption of calcium fluoride by SEM observation, and they were evaluated as "◯" (Table 1).

On the contrary, in the case of Comparative Example 1 comprising composition (X) containing calcium lactate, the amount of fluorine adsorption on the HAP pellet alternately treated by composition (X) and composition (Y) was 20 mg/m$^2$.

Here, while the amount of fluorine adsorption on the HAP pellet was 28 mg/m$^2$ in Example 2 although only 0.5 wt. % of calcium lactate was contained in composition (X), the amount of fluorine adsorption on the HAP pellet in Comparative Example 1, which was alternately treated by composition (X) containing 1 wt. % of calcium lactate and composition (Y), was 20 mg/m$^2$ on the contrary and therefore it had an adsorption amount lower than the case of Example 2.

This is because the calcium fluoride fine particle (the primary particle) formed by calcium lactate in the composition (X) and sodium fluoride in the composition (Y) was inhibited to form the secondary particle by containing 0.5 wt. % of glycerophosphate in the case of Example 2. Because of the effect of glycerophosphate to inhibit formation of the secondary particle, calcium fluoride fine particles which were the primary particles came to be present in large amounts, and such fine particles (the primary particle) efficiently adsorbed on the HAP pellet, and as a consequence, thus obtaining a high amount of fluorine adsorption to the extent of 28 mg/m$^2$.

On the contrary, in the case of Comparative Example 1, because of composition (X) containing only calcium lactate, an alternate treatment using calcium lactate in the composition (X) and sodium fluoride in composition (Y) formed the calcium fluoride fine particles (the primary particle), and thereafter progressed the aggregation to form secondary particles having a large particle size rapidly out of control. Such secondary particle having a large particle size was not so efficient in adsorption on the HAP pellet, and as a consequence, the amount of fluorine adsorption became 20 mg/m$^2$, which was a lower value than that of Example 2.

Moreover, in the case of subjecting to an alternate treatment by composition (X) containing only calcium glycerophosphate and composition (Y) containing sodium fluoride such as in Comparative Example 2, the formation of the primary particle of calcium fluoride was slow (see FIG. 1), and as a consequence, the amount of fluorine adsorption on the HAP pellet became 14 mg/m$^2$.

In the case of subjecting to an alternate treatment by the composition (X) containing only sodium monofluorophosphate and the composition (Y) containing sodium fluoride in Comparative Example 3, the formation of the primary fine particle of calcium fluoride was not recognized.

Adsorptive states of calcium fluoride observed by the SEM were shown in Table 1. In Comparative Example 1 and Comparative Example 2, the state of some adsorption of calcium fluoride could be verified, and it was evaluated as "Δ". In Comparative Example 3, the state of little adsorption of calcium fluoride could be verified, and it was evaluated as "X".

b. The State of Adsorption of Calcium Fluoride Fine Particles on HAP Powder

Figure 2:
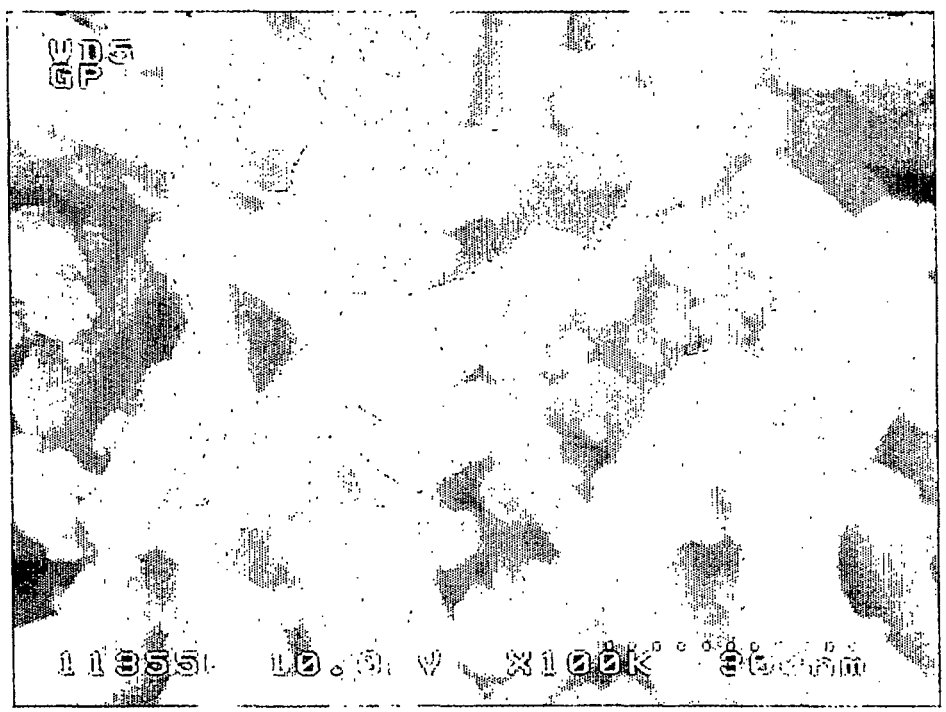
FIG. 2 shows an adsorbed state on HAP powder in Example 1.

FIG. 2 is the SEM photograph showing the adsorptive state of calcium fluoride fine particle on the HAP powder treated by compositions (X) and (Y) in Example 1. In FIG. 2, it could be verified that small granules were adsorbed on the rod-like HAP powders. The granules were calcium fluoride fine particles, and they were mainly secondary particles.

Figure 3:
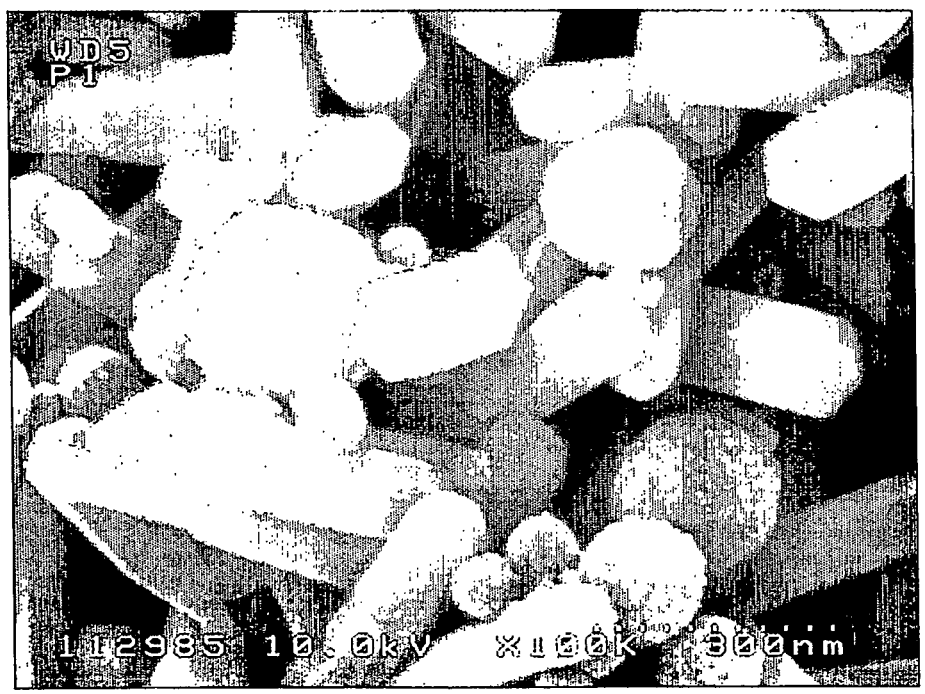
FIG. 3 shows an adsorbed state on HAP powder in Comparative Example 1.

FIG. 3 shows the adsorptive state of calcium fluoride fine particles on HAP powder treated by compositions (X) and (Y) in Comparative Example 1. In FIG. 3, the secondary particles which are larger than Example 1 (FIG. 2) on the rod-like HAP powders could be verified.

Figure 4:
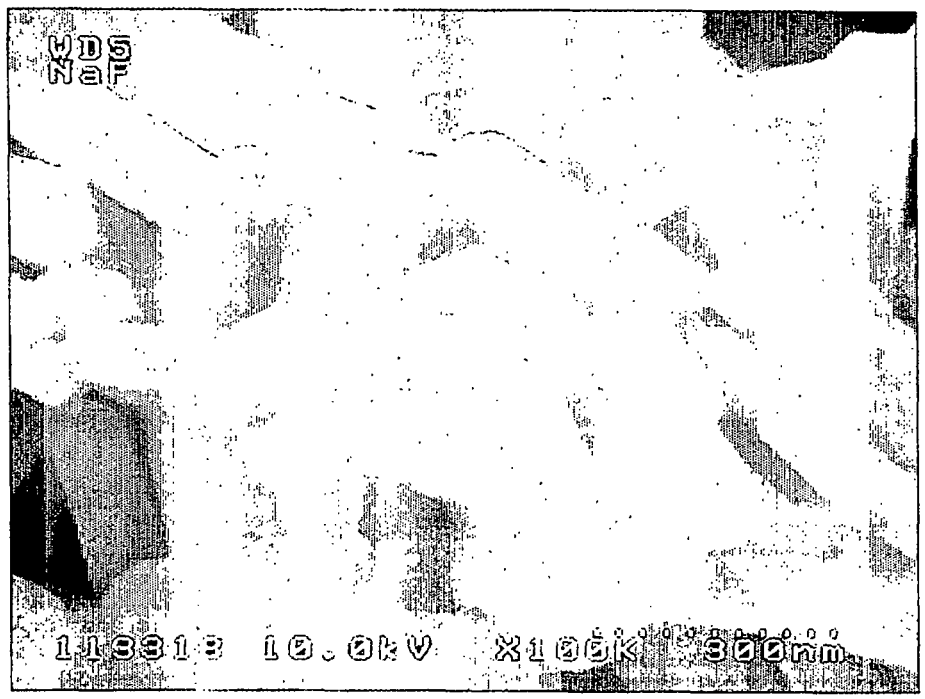
FIG. 4 shows an adsorbed state on HAP powder in Comparative Example 3.

Production of the large size secondary particles is owing to rapid proceeding of the secondary aggregation with no control of or no retardation of proceeding thereof due to no presence of glycerophosphate The adsorptive state of calcium fluoride fine particles on the HAP powder treated by compositions (X) and (Y) in Comparative Example 3 is shown in FIG. 4. As shown in FIG. 4, the calcium fluoride fine particles could hardly be verified on the HAP powder in Comparative Example 3. Because, in the case of subjecting to an alternate treatment by composition (X) containing only sodium monofluorophosphate (see Table 1) and composition (Y) containing sodium fluoride, the calcium fluoride fine particles were hardly be formed.

c. Change of Turbidity after Mixing Composition (X) and Composition (Y)

The change of turbidity after mixing two compositions (X) and (Y) is shown in FIG. 1. Here, the turbidity (the absorbance at 600 nm) reflects the state of formation of calcium fluoride fine particles (the secondary particle). As shown in FIG. 1, in the case of Example 1, the absorbance rose rapidly immediately after mixing of composition (X) and composition (Y), and then gradually diminished. This means the particle size was controlled after calcium fluoride fine particles were rapidly formed.

Figure 5:
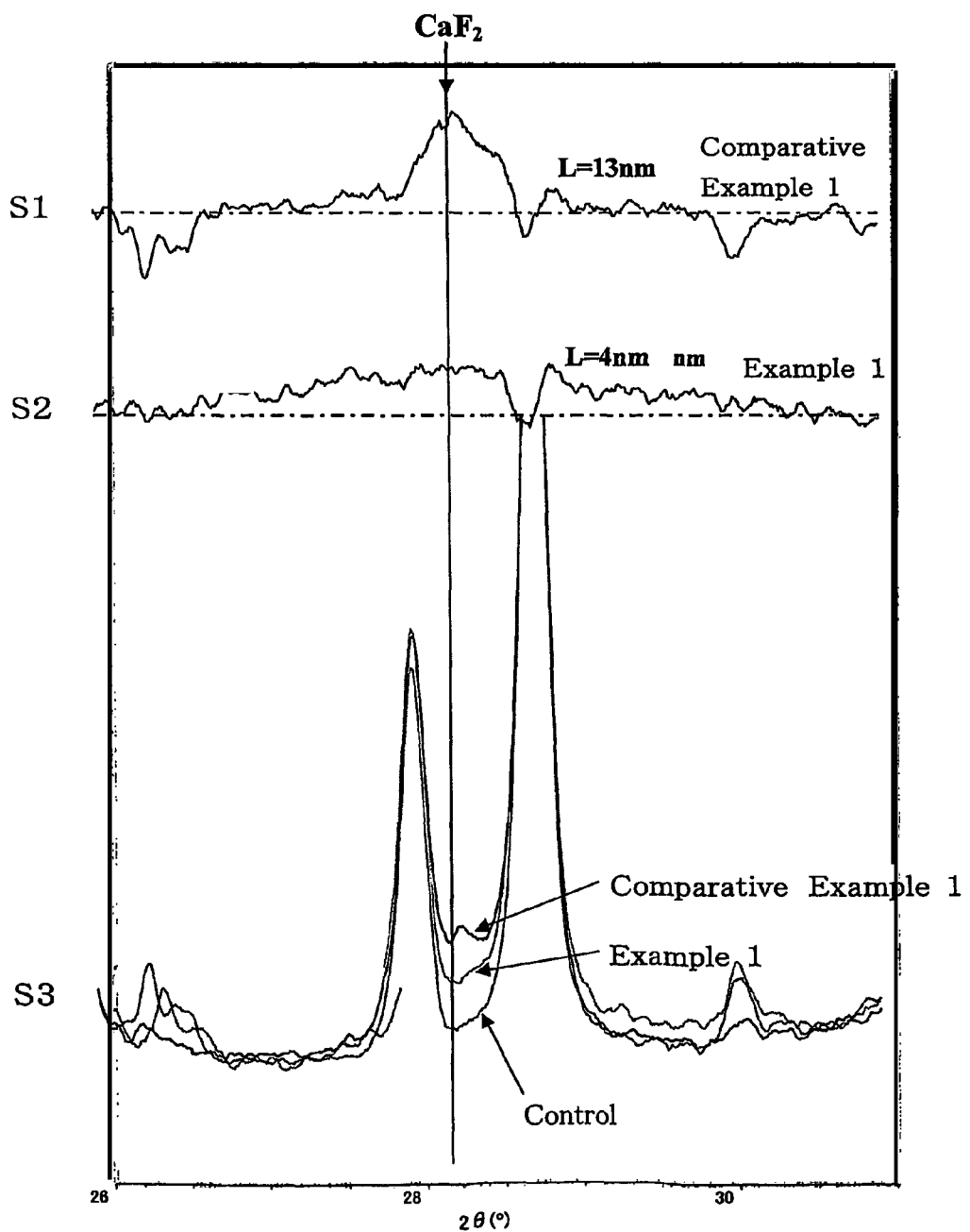
FIG. 5 shows a result of measurements of the crystal size of calcium fluoride by X-ray diffraction.

On the contrary, in the turbidity after mixing of composition (X) and composition (Y) in Comparative Example 1, the absorbance showed a tendency to rise over time for 10 seconds immediately after mixing. This shows the normal formation behavior of a calcium fluoride fine particle. Additionally, in Comparative Example 2 (the composition of Japanese Patent Laid-Open No. Hei 10-511956), the rise of absorbance could hardly be verified for about 10 seconds after mixing of composition (X) and composition (Y). This means that the formation of calcium fluoride fine particles was inhibited.

d. Analysis of Size of Calcium Fluoride Primary Particle (Crystal Particle) by X-Ray Diffraction The presence of $CaF_2$ could be verified by peaks of d=3.1546(111), d=2.7314(200) and d=1.9316(220) that were diffraction peaks of $CaF_2$ (PDF# 35-0816). The spectra only near d=3.1546 was shown in FIG. 5. The attention was focused on the area of d=3.1546(111) of $CaF_2$ that could be separated most easily without overlapping with the peak of hydroxyapatite, and the difference of strength between the diffraction peaks of HAP powder treated by various treatments and the diffraction peak of untreated HAP powder (control) were determined respectively in the range of 26.0 to 31.0 degrees of 2 theta (2θ). And then peaks of only $CaF_2$ were separated (S1 and S2 in FIG. 5). Using the diffraction angle and the half-width (width at half of peak height) of such separated peaks ($CaF_2$), the crystal size (Å: angstrom) was calculated by Scherrer's equation (D=Kλ/B·cos θ), wherein coefficient K=0.9, CuKα λ=1.54056 angstrom, B: half-width of peak (width at half of peak height (rad)), θ: diffraction angle (position of peak top).

As a result, the crystal size in Example 1 was 4 nm, and the crystal size in Comparative Example 1 was 13 nm.

e. Analysis of the Component of the Calcium Fluoride Secondary Particle

In the HAP powder sample treated by the compositions in Example 1, carbon was detected from the results of SEM-EDS measurement, and it could be verified the carbon derived from glycerophosphate was adsorbed on it.

In the HAP powder sample treated by the composition in Example 1, the desorption peak of fluorine was derived from decomposition above near 400° C. from the results of 19F measurement by mass spectrometry of temperature-programmed desorption method (TPD). On the other hand, in the HAP powder sample treated by the composition in Comparative Example 1, the desorption peak of fluorine derived from decomposition was not obtained above near 400° C. That is, it could be verified from the HAP powder sample treated by the composition in Comparative Example 1 that calcium fluoride was stable and never decomposed, and it could be verified that fluorine detected in the HAP powder sample treated by the composition in Example 1 was derived from monofluorophosphate.

From the results of the above analyses, it could be verified that both glycerophosphate and monofluorophosphate were adsorbed on the HAP powder sample treated by the compositions in Example 1, and the values of quantitative determination by ion chromatography were 1.0 wt. % of monofluorophosphate and 2.9 wt. % of glycerophosphate.

f. Effect of Inhibiting Demineralization

Figure 6:
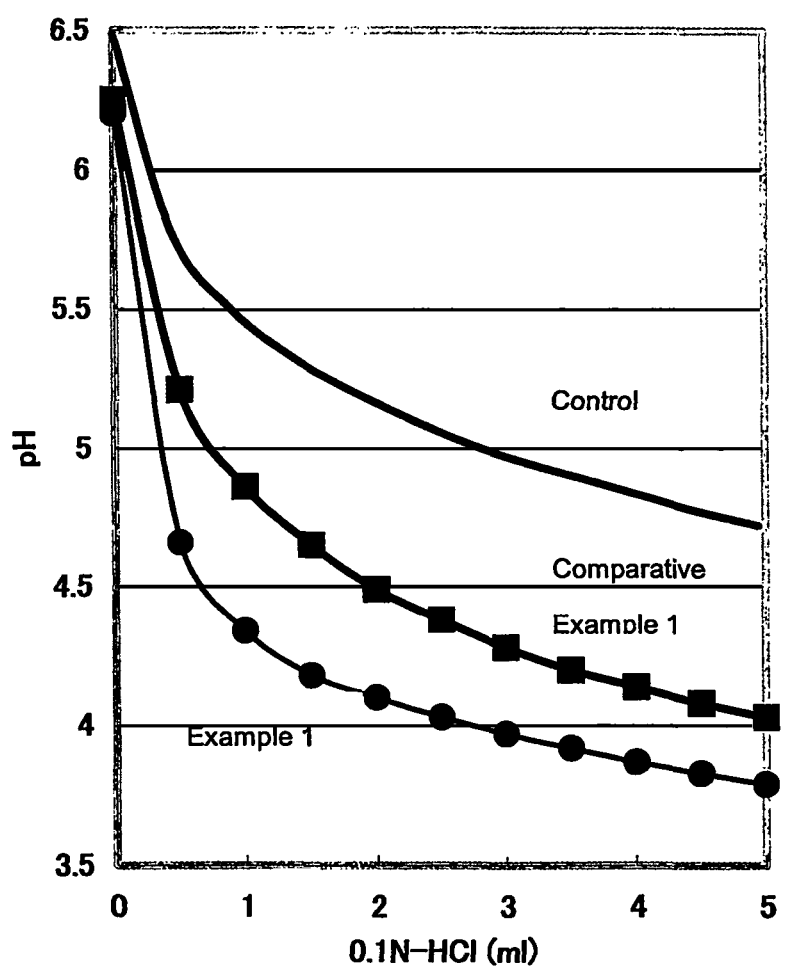
FIG. 6 shows changes of pH caused by titration of HAP in an Example and Comparative Examples.

The result of potentiometric titration is shown in FIG. 6. If phosphate ions or calcium ions are eluted from teeth (i.e. demineralization), the concentration of phosphate ions or calcium ions in the solution will increase, and the change of pH when hydrochloric acid is added will diminish. If the elution of phosphate ions or calcium ions from teeth is inhibited, the concentration of phosphate ions or calcium ions in the solution will be low, and the pH value of the solution will change significantly by additional hydrochloric acid. The evaluation of effect of inhibiting demineralization of mouthwash is based on this principle.

As shown in FIG. 6, the HAP powder with no treatment was dissolved below about pH 5.5, but the HAP powder in Example 1 was dissolved below about pH 4.5, and the HAP powder in Comparative Example 1 was dissolved below about pH 5.1. This means the treatment by the composition in Example 1 has a more excellent effect of inhibiting demineralization than the treatment by the composition in Comparative Example 1.

2. Dentifrices (1) Preparation of Dentifrices

Two compositions, namely composition ($X_1$) containing calcium glycerophosphate and sodium monofluorophosphate and composition ($Y_1$) containing sodium fluoride were prepared respectively according to the compositions as shown in Tables 2 and 3. Then each of the prepared compositions was put in each compartment of a dentifrice container made of a tube inside of which is divided by a partition so as to allot one composition to one compartment separately at equal amounts per composition.

TABLE 2

| Composition ($X_1$) | (wt. %) |
| --- | --- |
| Sodium monofluorophosphate | 0.72 |
| Calcium glycerophosphate | 1 |
| Sorbit solution (70 wt. % solution) | 40 |
| Calcium carbonate *2 | 15 |
| Polyethyleneglycol 600 | 4 |
| Citric acid | 0.1 |
| Sodium saccharate | 0.1 |
| Sodium lauryl sulfate | 1.2 |
| Silicic acid anhydride | 7 |
| Sodium carboxymethyl cellulose | 1 |
| Flavor | 1 |
| Purified water | balance |
| Total | 100 |

*2; mean particle size: 150 micrometers

TABLE 3

| Composition ($Y_1$) | (wt. %) |
| --- | --- |
| Sodium fluoride | 0.21 |
| Xylitol | 9 |
| Sorbit solution (70 wt. % solution) | 32 |
| Polyethyleneglycol 600 | 4 |
| Sodium saccharate | 0.1 |
| Sodium lauryl sulfate | 1.2 |
| Silicic acid anhydride | 20 |
| Sodium carboxymethyl cellulose | 1.5 |
| Flavor | 1 |
| Purified water | balance |
| Total | 100 |

Two compositions, namely composition ($X_2$) containing calcium glycerophosphate and sodium monofluorophosphate and composition ($Y_2$) containing sodium fluoride were prepared respectively according to the compositions as shown in Tables 4 and 5. Then each of the prepared compositions was put in each compartment of a dentifrice container made of a tube inside of which is divided by a partition so as to allot one composition to one compartment separately at equal amounts per composition.

TABLE 4

| Composition ($X_2$) | (wt. %) |
| --- | --- |
| Sodium monofluorophosphate | 0.72 |
| Calcium glycerophosphate | 0.7 |
| Sorbit solution (70 wt. % solution) | 35 |
| Calcium lactate | 0.5 |
| Lactic acid | 0.3 |
| Polyethyleneglycol 600 | 4 |
| Xylitol | 6 |
| Sodium saccharate | 0.1 |
| Sodium lauryl sulfate | 1.2 |
| Silicic acid anhydride | 17 |
| Sodium carboxymethyl cellulose | 0.9 |
| Carrageenan | 0.2 |
| Xanthan gum | 0.2 |
| Flavor | 1 |
| Purified water | balance |
| Total | 100 |

TABLE 5

| Composition ($Y_2$) | (wt. %) |
| --- | --- |
| Sodium fluoride | 0.21 |
| Xylitol | 6 |
| Sorbit solution (70 wt. % solution) | 35 |
| Polyethyleneglycol 600 | 4 |
| Sodium saccharate | 0.1 |
| Sodium lauryl sulfate | 1.2 |
| Silicic acid anhydride | 17 |
| Sodium carboxymethyl cellulose | 0.9 |
| Carrageenan | 0.2 |
| Xanthan gum | 0.2 |
| Flavor | 1 |
| Purified water | balance |
| Total | 100 |

(2) Evaluation of Oral Preparation System
<1> Effect of Remineralization
A. Material and Method
1) Preparation of Demineralized Tooth An extracted human molar was used as a tooth specimen. The enamel section of the tooth specimens having a window with a size of 3 mm×3 mm thereon was soaked in a 0.1M lactate buffer solution (pH:4.5) at 37° C. for three days to form an artificially demineralizing lesion beneath the surface.

2) Remineralization Treatment of Tooth in a Human Oral Cavity

Said demineralized teeth were fixed in the oral cavities of 10 healthy 30 to 40 year-old adult examinees by stents made of resin and fitted with a buccal dental arch of mandible.

(i) Dentifrices for Remineralization Treatment of Tooth

Dentifrices to be used for remineralization treatment of tooth were as follows: the dentifrice in Example 3 as the dentifrice of the two-agent type, wherein composition ($X_1$) containing calcium glycerophosphate and sodium monofluorophosphate and composition ($Y_1$) containing sodium fluoride were put in an united container inside of which was divided into two compartments by a partition so as to allot one composition to one compartment in an amount ratio of 1:1; the dentifrice in Comparative Example 5, wherein only composition ($X_1$) in Table 2 was put in a container having single compartment; the dentifrice in Comparative Example 4, wherein composition ($Y_1$) in Table 3 was put in another container having single compartment.

(ii) Usage of Dentifrices

The dentifrices in Example 3, Comparative Example 4, and Comparative Example 5 were used by the examinees respectively.

Figure 7:
FIG. 7 shows a state attaching a segment of an incipient caries.

As shown in FIG. 7, the stent was attached to the oral cavity of the examinee for 24 days, and the dentifrice was used by the examinee thrice a day in the usual manner. Thereafter, the stent was detached from the oral cavity, and the sample segment was detached. In the identical examinee, according to the aforementioned method, a set of 24 days was repeatedly conducted three times.

3) Measurement of Remineralization of Tooth by Contact Microradiography (CMR)

After the remineralization treatment, each of the sample segments was cut and formed a polished segment with thickness of about 150 micrometers, and was photographed by CMR; The obtained CMR image (soft X-ray photograph) was analyzed by image analysis, and the amount of loss of mineral ($\Delta Z$) was measured. Here, it is to be noted that $\Delta Z$ is the product (vol %·micrometers) of the concentration of the demineralized section and the demineralized depth from the surface.

Moreover, the rate (%) of mineral recovery of the group using respective dentifrices was evaluated by the following formula;

$$\{(\Delta Z \text{ before reminelarization treatment (baseline)} - \Delta Z \text{ after reminelarization treatment})/\Delta Z \text{ before reminelarization treatment (baseline)}\} \times 100$$

A higher value of the rate (%) of mineral recovery means a higher level of remineralization.

B. Result

Figure 8:
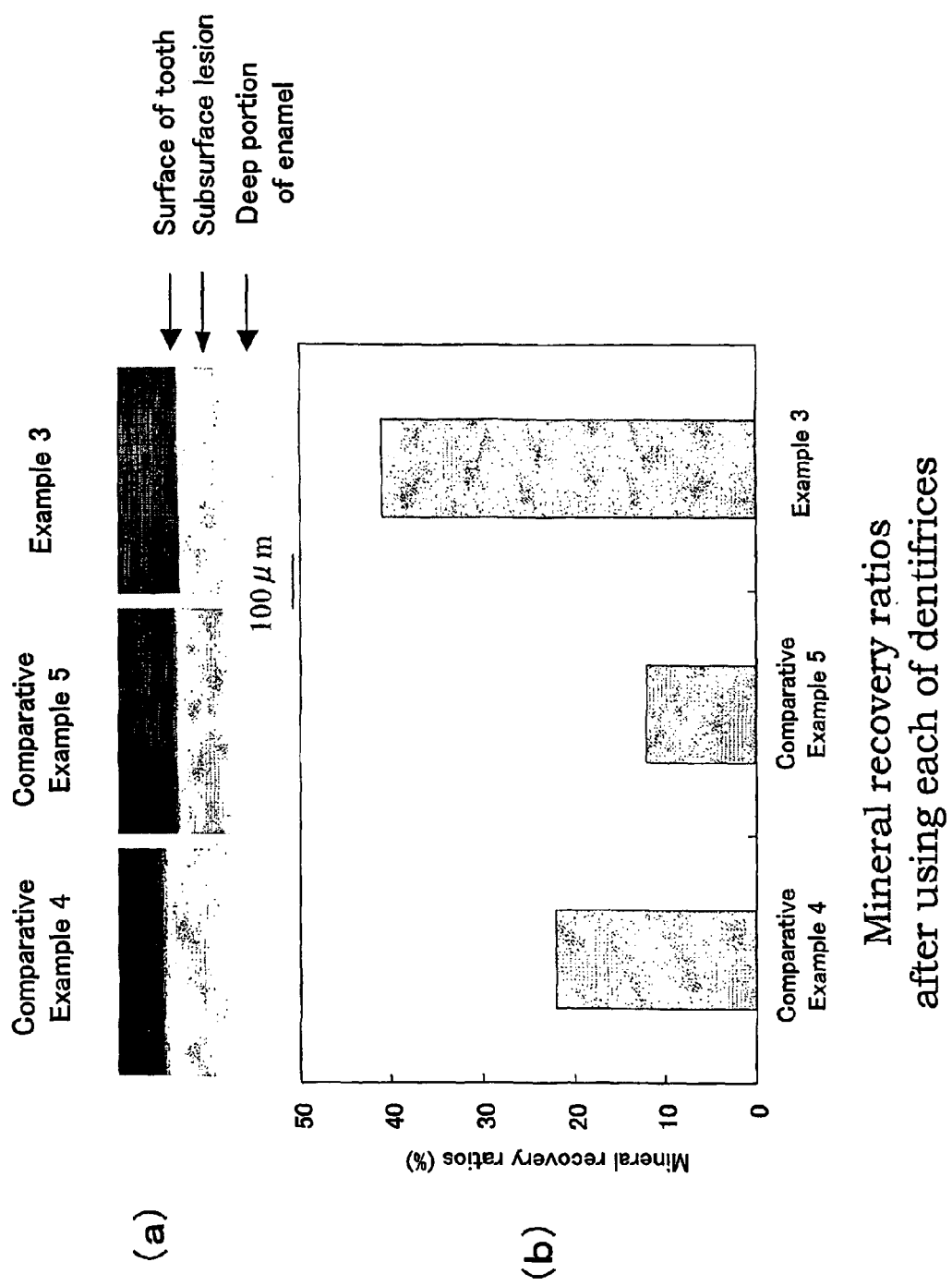
FIG. 8(a) shows CMR (soft X-ray) photographs taking the section of teeth.
FIG. 8(b) shows mineral recovery ratios of an Example and Comparative Examples.

FIG. 8(a) shows a microradiograph photographing a section of tooth. In FIG. 8(a), it was recognized that there was a gray part between the surface of the tooth and the deep portion of enamel. The lighter gray part means a better condition of mineral recovery in the tooth. In FIG. 8(a), it could be verified that the tone of the gray part in Example 3 is lightest of the three. This means that the effect of remineralization in Example 3 is higher compared to Comparative Example 4 and Comparative Example 5.

As shown in FIG. 8(b), in all groups using dentifrices of the Comparative Example 4, the Comparative Example 5, and the Example 3, it could be verified that ΔZ significantly decreases (progress of remineralization) compared to the demineralized tooth. The rate (%) of mineral recovery calculated from ΔZ were 22% in the group using dentifrices of the Comparative Example 4, 12% in the group using dentifrices of the Comparative Example 5, and 41% in the group using dentifrices of the Example 3. It could be verified that the oral preparation system of the present invention, used for the group using dentifrices of Example 3, had the highest effect of accelerating remineralization.

<2> Effect of Suppressing pH Decrease Due to Residual Plaque

A. Material and Method

The dentifrices used for the evaluation of the effect of suppressing pH decreases were prepared as follows. As the dentifrice in Example 4, the dentifrice of the two-agent type making a combination of composition ($X_2$) containing calcium glycerophosphate and composition ($Y_2$) containing sodium fluoride, wherein sodium monofluorophosphate was further contained in composition ($X_2$), was used. As the dentifrice in Comparative Example 6, only composition ($Y_2$) containing only sodium fluoride was used.

About 1 g of the dentifrice of Example 4 was used for 1 minute by the examinee who had brought the oral cavity cleaning to a halt for 2 days. And immediately after that, the plaque was collected. 30 mg of the collected plaque was added to 1 ml of suspended 5% sucrose solution, and was kept at 37° C. for 10 minutes. After that, the change of pH was repeatedly measured at intervals of 10 minutes. The dentifrice of Comparative Example 6 was used for the examinee in the same manner as the foregoing, and the change of pH was measured using the collected plaque according to the above method.

B. Result

While the pH of plaque after using the dentifrice of Example 4 changed from pH 6.8 to pH 6.4 after the lapse of 10 minutes, the pH of plaque after using the dentifrice of Comparative Example 6 changed from pH 6.8 to pH 5.4 after the lapse of 10 minutes. Namely, it could be verified that the change of pH of the residual plaque after using the dentifrice of Example 4 was smaller than Comparative Example 6, and the pH decrease of the residual plaque was suppressed by the use of dentifrice of Example 4. It could be assumed that effect of suppressing pH decrease by residual plaque was achieved because glycerophosphates having a pH buffering ability derived from the dentifrice of Example 4 was incorporated into the secondary particle of calcium fluoride at the time of forming calcium fluoride.

The invention claimed is:

1. A multi-composition oral preparation system comprising the following components:
   a first composition comprising:
   (A) a calcium ion supplying compound in an amount allowing a concentration of the calcium ion in the first composition to be from 1.25 to 400 μmol/g,
   (C) a polyolphosphate ion supplying compound in an amount allowing a concentration of the polyolphosphate ion in the first composition to be from 1.25 to 400 μmol/g, and
   (D) a monofluorophosphate ion supplying compound in an amount allowing a concentration of the monofluorophosphate ion in the first composition to be from 2.6 to 210 μmol/g, and
   a second composition comprising:
   (B) a fluoride ion supplying compound, other than a monofluorophosphate ion supplying compound, in an amount allowing a concentration of the fluoride ion in the second composition to be from 2.6 to 210 μmol/g,
   wherein the components (A) and (B) are separated within the oral preparation system, and
   the second composition does not comprise a phosphate ion supplying compound, and wherein said polysphosphate ion supplying compound is at least one of calcium polyolphosphates selected from the group consisting of calcium glycerophosphate, calcium glucose-1-phosphate and calcium glucose-6-phosphate.

2. The oral preparation system according to claim 1, wherein components (A), (B), (C) and (D) are admixed within the oral cavity or immediately prior to introduction into the oral cavity.

3. The oral preparation system according to claim 2, wherein calcium fluoride fine particles are formed upon admixture of all the components.

4. The oral preparation system according to claim 3, wherein the calcium fluoride fine particle has a primary particle size of from 0.3 to 15 nm.

5. The oral preparation system according to claim 3, wherein a secondary particle is formed from an aggregate of the calcium fluoride fine particles, wherein the secondary particles comprise monofluorophosphates and/or polyolphosphates.

6. The oral preparation system according to claim 5, wherein the content of the monofluorophosphates is in the range of from 0.05 to 20% by weight of the secondary particle, and the content of the polyolphosphates is in the range of from 0.05 to 20% by weight of the secondary particle.

7. The oral preparation system according to claim 1, wherein the calcium ion supplying compound is at least one of calcium polyolphosphates selected from the group consisting of calcium glycerophosphate, calcium glucose-1-phosphate, and calcium glucose-6-phosphate.

8. A multi-composition oral preparation system comprising the following components:
   a first composition comprising:
   (D) a monofluorophosphate ion supplying compound in an amount allowing a concentration of the monofluorophosphate ion in the first composition to be from 2.6 to 210 μmol/g, and
   (E) calcium polyolphosphate in an amount allowing a concentration of each of the calcium ion and the polyolphosphate ion in the first composition to be from 1.25 to 400 μmol/g, and a second composition comprising:
(B) a fluoride ion supplying compound, other than a monofluorophosphate ion supplying compound, in an amount allowing a concentration of the fluoride ion in the second composition to be from 2.6 to 210 μmol/g,
wherein the components (B) and (E) are separated within the oral preparation system, and
the second composition does not comprise a phosphate ion supplying compound.

9. The oral preparation system according to claim 1, wherein the concentration of the calcium ion in the first composition is from 5 to 400 μmol/g.

10. A multi-composition oral preparation system comprising the following components:
a first composition comprising:
(A) a calcium ion supplying compound in an amount allowing a concentration of the calcium ion in the first composition to be from 1.25 to 400 μmol/g, and
(C) a polyolphosphate ion supplying compound in an amount allowing a concentration of the polyolphosphate ion in the first composition to be from 1.25 to 400 μmol/g,
and
a second composition comprising:
(B) a fluoride ion supplying compound, other than a monofluorophosphate ion supplying compound, in an amount allowing a concentration of the fluoride ion in the second composition to be from 2.6 to 210 μmol/g, and
(D) a monofluorophosphate ion supplying compound in an amount allowing a concentration of the monofluorophosphate ion in the second composition to be from 2.6 to 210 μmol/g,
wherein components (A) and (B) are separated within the oral preparation system,
wherein said polysphosphate ion supplying compound is at least one calcium polyolphosphates selected from the group consisting of calcium glycerophosphate, calcium glucose-1-phosphate and calcium glucose-6-phosphate.

11. The oral preparation system according to claim 10, wherein the concentration of the calcium ion in the first composition is from 5 to 400 μmol/g.

12. The oral preparation system according to claim 10, wherein calcium fluoride fine particles are formed upon admixture of all the components.

13. The oral preparation system according to claim 10, wherein the calcium fluoride fine particle has a primary particle size of from 0.3 to 15 nm.

14. The oral preparation system according to claim 10, wherein a secondary particle is formed from an aggregate of the calcium fluoride fine particles, wherein the secondary particles comprise monofluorophosphates and/or polyolphosphates.

15. The oral preparation system according to claim 10, wherein the content of the monofluorophosphates is in the range of from 0.05 to 20% by weight of the secondary particle, and the content of the polyolphosphates is in the range of from 0.05 to 20% by weight of the secondary particle.

* * * * *